United States Patent [19]

Schroeder

[11] 4,407,275

[45] Oct. 4, 1983

[54] ARTIFICIAL ERECTION DEVICE

[76] Inventor: William S. Schroeder, P.O. Box 607, Coos Bay, Oreg. 97420

[21] Appl. No.: 322,966

[22] Filed: Nov. 19, 1981

[51] Int. Cl.³ .............................................. A61F 5/42
[52] U.S. Cl. ...................................... 128/79; 128/60; 128/64
[58] Field of Search ...................... 128/32, 60, 64, 79, 128/327

[56] References Cited

U.S. PATENT DOCUMENTS

| | | | |
|---|---|---|---|
| 2,044,691 | 6/1936 | Hoflinger | 128/327 |
| 2,781,041 | 2/1957 | Weinberg | 128/60 |
| 3,495,589 | 2/1970 | Clement | 128/79 |
| 4,311,135 | 1/1982 | Brueckner et al. | 128/64 |

Primary Examiner—Dalton L. Truluck
Attorney, Agent, or Firm—Ted DeBoer

[57] ABSTRACT

A semi-rigid annular ring having individual expandable chambers on the internal wall that are distended separately by fluid pressure. A multi-port flexible conduit connected to the ring having individual ports for each chamber. Fluid pressure is supplied through the conduit manually by a bulb or electrically by a pump through a circular valve plate allowing the chambers to expand and contract in linear sequence. When a penis is placed into the ring and fluid pressure is applied, blood is forced to the end of the organ through the successive expansion and contraction of the bellows in wave fashion mechanically creating an erect condition of the organ.

7 Claims, 12 Drawing Figures

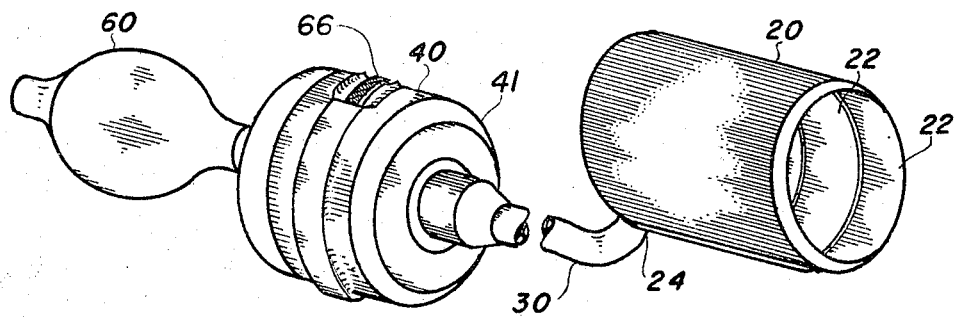
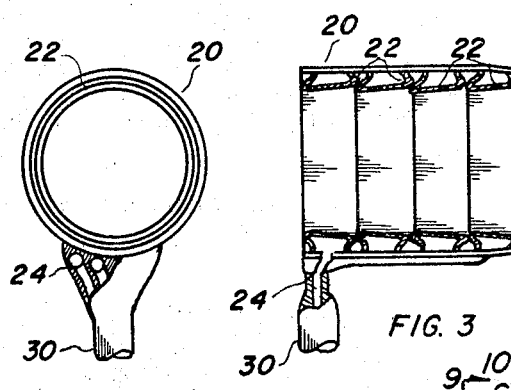
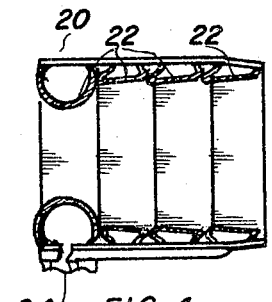
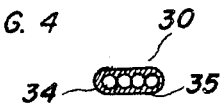
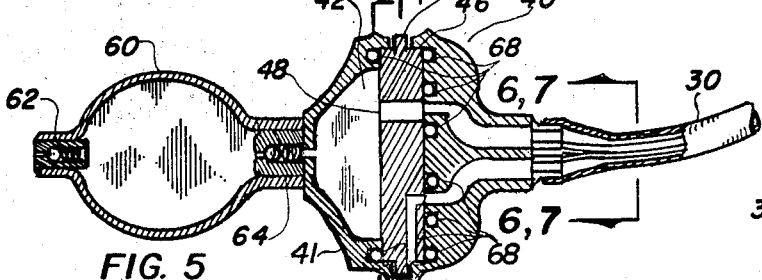
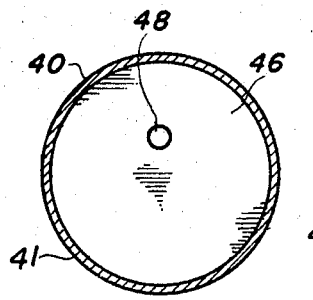
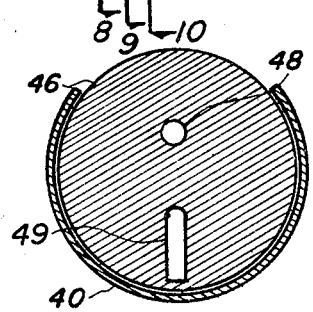
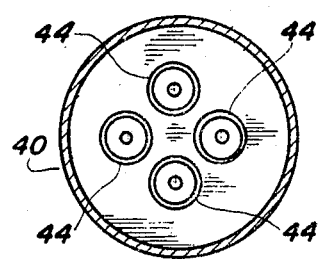

ARTIFICIAL ERECTION DEVICE

BACKGROUND OF THE INVENTION

1. Field of the Invention

This invention relates to medical instruments in general, more specifically for genital regions including tourniquets and prosthetic devices for use with the male sexual organ.

2. Description of the Prior Art

Previously, mechanical devices for collecting blood and maintaining the pressure in a penis have been limited to constricting devices that through diametrical reduction restrict the ventrical blood flow such an example is taught by Clement in U.S. Pat. No. 3,495,589. This approach to the problem simply surrounds the member and through pneumatic pressure limits the blood flow. It will be noted, however, that only the blood that is contained within the gland is pressurized as access is limited in arterial, as well as ventrical flow and no new blood is introduced. U.S. Pat. No. 2,044,691 issued to Hoflinger, discloses a device similar to the above, except a series of chambers are inflated in sequence with pneumatic pressure while fluid passes from one chamber to the other. These chambers all remain inflated at the same maximum pressure limiting the utility as in the above mentioned prior art. Sullinger in U.S. Pat. No. 3,461-863 teaches a simple tourniquet to maintain a voluntary penis erection by applying even localized pressure circumferentially around the root of the penis, however, this has no method of increasing the blood pressure or flow. U.S. Pat. No. 2,533,924 of Foley utilizes a ring with a localized inflatable chamber wth the utility being to close off the urethra under remote control. This device does not completely enclose the inside of a ring, but only partially blocks the periphery.

For background purposes and as indicative of the art to which the invention relates, reference may be made to U.S. Pat. No. 2,291,785 issued to Baudistel and 1,667,409 issued to Barr.

SUMMARY OF THE INVENTION

Numerous mechanical devices have been in existance for some time dealing with the problem of impotence in the male, due to advanced age, disease and psychological disorders resulting in the inability to accomplish a penial erection. Ordinarily the penis is erected when the dorsal veins are retracted and the dorsal and cavernosa arteries are extended, when erotically stimulated, allowing the blood to flow freely into the corpora cavernesa and corpus spongisium. The veinular restriction maintains the blood in the organ sustaining the erection. The primary object of this invention is to mechanically and remotely cause an erection by forcing the blood in the member to the extreme end and through a repeated contracting and dilating action utilize new blood supplied to the area as the device sequentially moves a restriction forward in wave action.

An important object provides not only an increase in blood pressure, but also an increased volume that may be replenished in order to maintain the desired result by re-energizing the system at any time.

Another object avoids the pain and pressure necrosis, due to continual pressure on the tissues as repeated dilation takes place in the device in the separate chambers and stops at an arbitrary location, not always the same one. Also, if this condition occurs, a simple actuation starts the system again stopping in most cases at another chamber relieving the discomfort.

Still another object provides for easy application and removal, as the pressure may be relieved deflating all of the chambers providing a smooth oversized conduit that is easily applied over the body member.

Yet another object allows the apparatus to be worn during coition and is so shaped to easily enter the vaginal canal with no harm or discomfort to the vaginal sheath.

A further object is to provide an apparatus having the above characteristics which is simple and easily operated by either partner, which allows ejaculation of semen during erection and maintains erection after orgasm.

Yet another object allows a mechanical device to be a substitute for an expensive surgical procedure.

BRIEF DESCRIPTION OF THE DRAWING

FIG. 1 is a partial isometric view of the preferred embodiment.

FIG. 2 is an end view of the annular ring with the conduit partially cut away showing the pneumatic passageways.

FIG. 3 is a cross sectional view of the annular ring with the expandable chambers deflated.

FIG. 4 is a cross-sectional view of the annular ring with only the first expandable chamber inflated.

FIG. 5 is a partial cut away elevation view of the sequential valve attached to the pneumatic pressure means and a portion of the flexible conduit.

FIG. 6 is a cross-section of the conduit taken along lines 6—6 of FIG. 5.

FIG. 7 is a cross-section of the conduit taken along lines 7—7 of FIG. 5.

FIG. 8 is a cross-sectional view of the sequential valve taken along lines 8—8 of FIG. 5.

FIG. 9 is a cross-sectional view of the sequential valve taken along lines 9—9 of FIG. 5.

FIG. 10 is a cross-sectional view of the sequential valve taken along lines 10—10 of FIG. 5.

DESCRIPTION OF THE PREFERRED EMBODIMENTS

Figure 11:
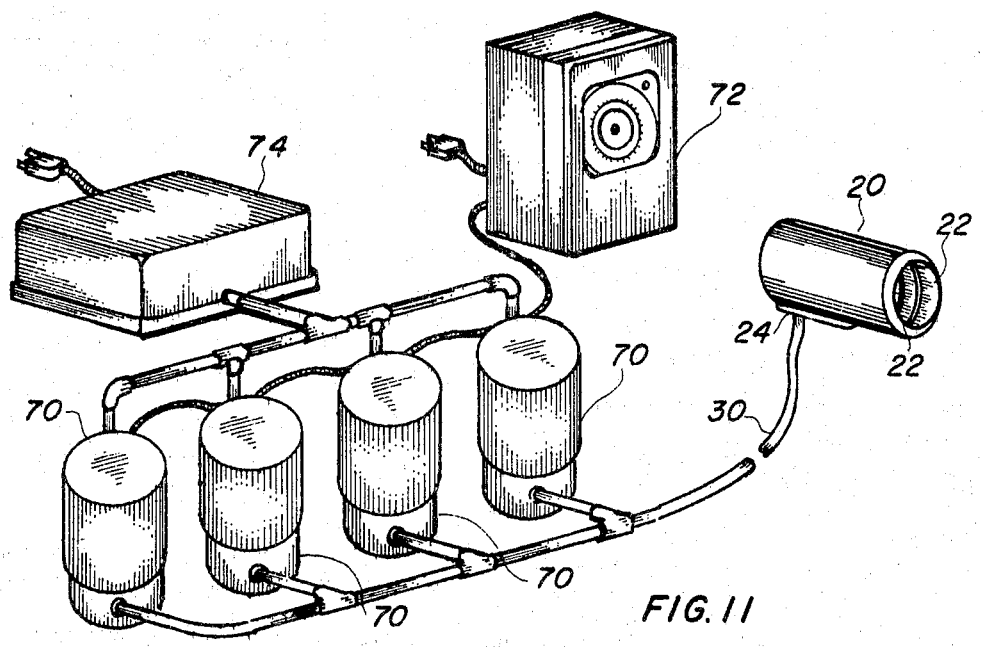
FIG. 11 is a partial isometric view of another embodiment having a pneumatic pump, solenoid valves and sequence timer switch along with the annular ring.

Referring now more specifically to the referenced characters of the drawings, the invention, in the preferred embodiment, utilizes a semirigid annular ring 20 with one end slightly tapered in truncated fashion forming a smooth transition. The ring further contains a plurality of individually expandable chambers 22 of flexible material that are formed in such a manner that when they are relaxed they retract to a flat nested position within the ring 20. The material of the ring 20 may be any suitable semi-rigid substance suitable for the application, such as synthetic rubber, nylon, latex, etc., with the chambers 22 of the same form, except completely flexible. Each chamber 22 is inflatable to decrease the inside diameter of the ring with the inside diameter, when deflated, somewhat smaller than an erect penis. The length of the ring 20 is substantially shorter than a relaxed penis and is easily slipped over the member when uninflated. An inner cover or sheath may be added to the interior surface if desired.

Each chamber 22 is ported separately to a central location 24 near the extreme end of the ring 20 where a multi-port flexible conduit 30 is attached. The configuration of this conduit may be either round 32 or flat 34 with the individual separated flow paths for each chamber grouped together. They are then covered with a circular sheath 33 still isolated from each other or separated side-by-side and covered by a flat sheath 35. Either configuration operating equally as well.

The other end of the conduit 30 is connected to a sequential valve 40 to divert intermittant pneumatic pressure in sequence to the ring 20 allowing only one chamber 22 to be pressurized at a given time. This operates with a common pressure chamber 42 in the valve body 41 on the entering air side and a plurality of segmented chambers 44 on the leaving air side with a rotatable circular valve plate 46 therebetween. This valve plate 46 is angularly extended about the central axis of the valve 40 and has an inlet port 48 completely through the structure parallel to the axis and a plate exhaust port 49 symmetrical with and 180 degrees from the inlet port 48, except it penetrates the outer periphery of the plate 46. The exhaust port 49 has one side in direct communication with one of the chambers 44 and the other is directed to atmosphere through the peripheral exposed edge, best shown in FIGS. 5 and 9. The plate 46 is flat on two parallel surfaces and is so formed that the outside circumference contains a raised ring 66 with a serated or knurled finish on the edge. The valve 40 is shaped to allow this knurled edge to protrude slightly beyond the surface in an indented depression of the valve body 41. The valve 40 is actuated by placing a bulb 60 in the hand and rotating the plate 46 with the thumb. The rotational movement of the plate 46 lines the inlet port 48 with one of the segmented chambers 44 allowing pressure to be released through the conduit 30 into the appropriate expandable chamber 22. When manually moved the plate 46 continues to rotate to a new segmented chamber 44 pressurizing the next chamber 22 in line while the plate exhaust port 49 then relieves the pressure through the opening in the valve 40 to atmosphere on the previously extended chamber 22. This movement of the sequenced pneumatic source creates a wave effect of the expanding and contracting chambers 22, creating the pumping action in linear fashion upon the penis.

Pneumatic pressure is supplied to the valve 40 by any source, such as a diaphram pump with electromotive actuation (not shown in this embodiment) with a switch to actuate the pump on and off for supplying compressed air, however, a flexible bulb or aspirator 60 is preferred. This bulb 60 is of resilient material such as latex, synthetic rubber, plastics or the like, the approximate size of ones hand and has an inlet check valve 62 on one end and a discharge outlet check valve 64 on the other. The outlet check valve 64 is attached to the pressure chamber 42. When the bulb 60 is squeezed by hand the inlet check valve 62 seals and pressure is built up inside passing through the outlet valve 64. When the hand pressure on the bulb is released, the inlet valve 62 opens and the outlet valve 64 close allowing fresh air to enter the bulb 60 to continue the pressurizing action. This valve arrangement allows pressure to the expandable chambers and the ports and chambers are sealed to each other with appropriate "O" rings 68 or friction seals, best illustrated in FIG. 5. It will be noted that any fluid or pneumatic source would be applicable in this invention and should not be limited to the above described bulb or pump.

Figure 12:
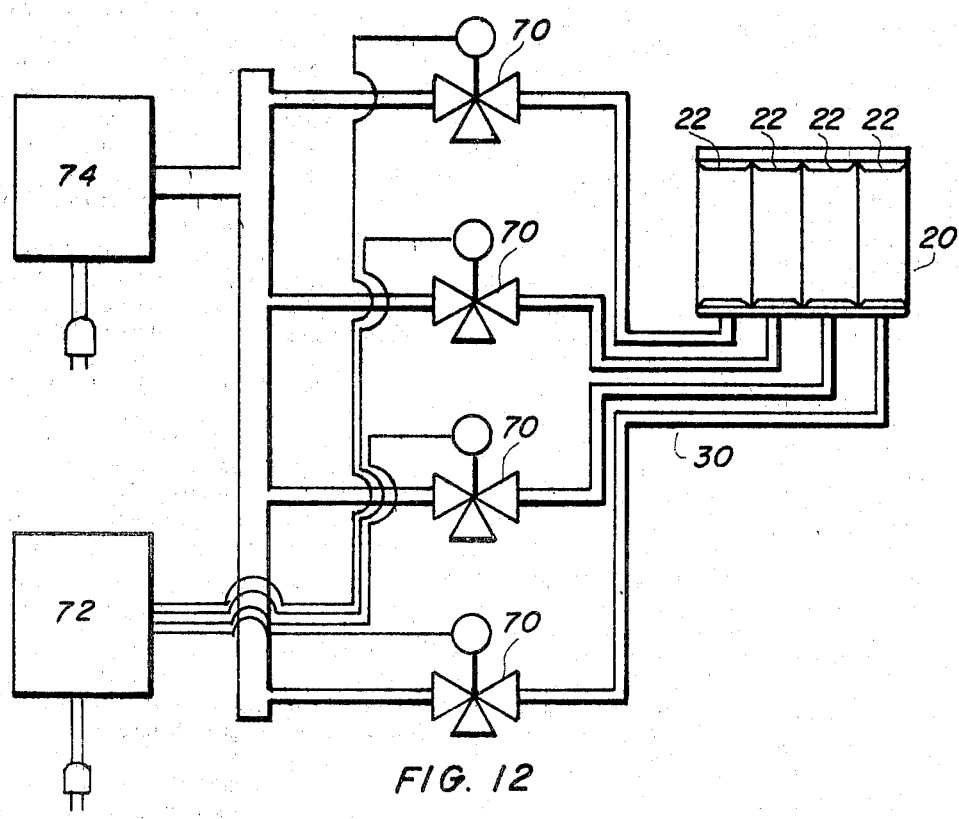
FIG. 12 is a pneumatic flow and electrical schematic of another embodiment having a pneumatic pump, solenoid valves and sequence timer switch.

In another embodiment, best depicted in FIGS. 11 and 12, the semi-rigid annular ring 20 is utilized along with the multi-port flexible conduit 30 in the same manner as above described, except a plurality of 3-way solenoid valves 70 are manifolded together and attached to the conduit 30 which allows each expandable chamber 22 to be separately inflated and relieved. The solenoid valve 70 includes an electrical coil surrounding a plunger creating an electromagnetic field that lifts the plunger with linear force off a seat in the valve to open the valve ports when energized. It is so configured that when it is electrically deenergized the pressure is relieved to atmosphere allowing the chamber 22 to be expanded only when electrical power is applied.

A manual or sequence timer switch 72 is electrically connected to the 3-way valves 70 that energized the valves in sequence at a given time and duration allowing pressure modulation and amplitude modulation by setting the sequence in shorter or longer time durations.

A pneumatic pump 74 supplies the pressure and is preferably the diaphram type, however, any low pressure source may be utilized. The pump 74 is manifolded to the valves 70 in a simple and direct method of tees or splitter Y's or individual lines from an integral pump manifold. The pump 74 is electrically actuated and may run continuously or cycled as required by the timer 72. Some configurations of pumps 74 may require a relief valve when all of the solenoids 70 are deenergized to eliminate a pressure build-up when operating at a dead head.

All of the above mentioned components, valves 70, pump 74 and timer 72 may be housed together for convenience, but are shown separated in FIG. 11 for clarity, also on-off switches and speed controls may be added for convenience of the operator.

Although the invention has been described in complete detail and pictorially shown in the accompanying drawings it is not to be limited to such details since many changes and modifications may be in the invention without departing from the spirit and scope thereof, hence it is described to cover any and all modifications and forms which may come within the language and scope of the appended claims.

What is claimed is:

1. A prosthetic device for increasing the blood pressure and volume in a penis creating or maintaining an erect condition comprising:
    a. a semi-rigid annular ring having a plurality of flexible individually expandable chambers therein, the inside diameter somewhat smaller than said erect penis with the length substantially shorter, the inside surface planar with said ring when said chambers are relaxed;
    b. a multi-port flexible conduit connected to said individual expandable chambers allowing a separated flow path for each chamber while grouping together in one conduit;
    c. a ratcheted sequential valve attached to said annular ring with said multi-port flexible conduit for diverting intermittent pneumatic pressure in sequence from a pulsating source to said ring allowing only one chamber to be pressurized at a given time, also a manual valve mechanism to depressurize said chamber when unwanted; and, d. a flexible bulb creating pneumatic pressure means attached to said valve for providing compressed air to the apparatus in pulsating fashion having an inlet check valve and a first and second outlet check valve, being of a size to fit into ones hand and actuated by squeezing, therefore, increasing the air pressure contained within said inlet check valve providing a one-way inlet path for continuing the source of the pneumatic pressure, said first outlet check valve being disposed with said ratcheted sequential valve for the bellows actuator to supply one-way air thereto, and said second outlet check valve also connected to said ratcheted sequential valve for sequenced one-way direction to said expandable chambers for sequencing said valve and inflating said chamber.

2. The prosthetic device, as recited in claim 1, wherein said annular ring further comprises:

an outer ring of semi-rigid structure having a first end and a second end and a plurality of individually expandable chambers attached therein with the first end tapered slightly in truncated fashion forming a smooth transition and the second end having an interface connection for said flexible conduit with a tubular passageway and inlet port into each expandable chamber for direct communication with said conduit and valve to allow expansion of the appropriate chamber by pressure from said valve.

3. The prosthetic device of claim 1, wherein said flexible conduit further comprises:

a circular sheath with the individual ports separated therein and isolated from each other.

4. The prosthetic device of claim 1, wherein said flexible conduit further comprises:

a flat sheath with the individual ports separated side-by-said and isolated from each other.

5. The prosthetic device sequential valve, as cited in claim 1, further comprising:

a housing defining a central axis;

a circular valve plate rotatably positioned within said housing annularly extending about the axis defining an inlet port therethrough parallel to said axis and an exhaust port symmetrical with and opposite said inlet port, except penetrating the outer exposed surface with the periphery of the plate extending beyond said housing allowing rotation by ones thumb, therefore, sequencing pressure from said pressure means to said annular ring chambers and releasing pressure therefrom.

6. The prosthetic device pressure means of claim 1, further comprising:

a diaphram pump with electromotive actuation and switch means to actuate the pump on and off supplying compressed fluid.

7. A prosthetic device for increasing the blood pressure and volume in a penis creating an erect condition comprising:

a. a semi-rigid annular ring having a plurality of flexible individually expandable chambers therein, the inside diameter somewhat smaller than said erect penis with the length substantially shorter, the inside surface planar with said ring when said chambers are relaxed;

b. a multi-port flexible conduit connected to said individual expandable chambers allowing a separated flow path for each chamber while grouping together in one conduit;

c. a plurality of three-way valves manifolded together and attached to said flexible conduit for inflating said expandable chambers individually, with each valve having an inlet, outlet and exhaust port, also an electrical solenoid for operating said valve by creating an electromagnetic field around a plunger with linear force moving the plunger off of a seat to actuate said ports;

d. a sequence timer switch electrically connected to said three-way valves to energize said valves in sequence at a given time and duration, and;

e. a pneumatic pump connected to said valve manifold supplying compressed air through said valve and flexible conduit to said expandable chambers, causing sequential expanding and contracting in wave fashion forcing blood in a penis placed therein from the lower port surrounded by said annular ring to the end opposite said ring increasing blood pressure and causing volumetric enlargement of said body member.

* * * * *